United States Patent [19]

Mauz et al.

[11] 4,024,267
[45] May 17, 1977

[54] SUBSTITUTED HYDROXYPHENYL-PIPERIDONES

[75] Inventors: Otto Mauz, Liederbach, Taunus; Ernold Granzer, Kelkheim, Taunus, both of Germany

[73] Assignee: Hoechst Aktiengesellschaft, Frankfurt am Main, Germany

[22] Filed: July 9, 1975

[21] Appl. No.: 594,437

[30] Foreign Application Priority Data

July 11, 1974   Germany ............................ 2433234

[52] U.S. Cl. ............................ 424/267; 260/293.76
[51] Int. Cl.$^2$ ...................................... A61K 31/445
[58] Field of Search ................ 260/293.76; 424/267

[56] References Cited

UNITED STATES PATENTS 2,524,643   10/1950   Walter et al. ................. 260/293.76

FOREIGN PATENTS OR APPLICATIONS 1,958,424   5/1971   Germany

OTHER PUBLICATIONS

Chemical Abstracts, vol. 54 (1960) 3264b.

*Primary Examiner*—Norma S. Milestone
*Attorney, Agent, or Firm*—Curtis, Morris & Safford

[57] ABSTRACT

Piperidone derivatives of the formula

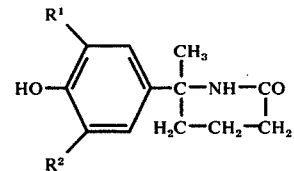

in which $R^1$ and $R^2$, which may be identical or different, each represent a hydrogen atom or a halogen atom or an alkyl or alkoxy group of 1 to 9 carbon atoms, process for preparing them and pharmaceutical preparations consisting of, or containing, these compounds.

4 Claims, No Drawings

SUBSTITUTED HYDROXYPHENYL-PIPERIDONES

The present invention relates to 6-(4-hydroxyphenyl)-6-methyl-piperidone-(2) and to its derivatives of the formula I

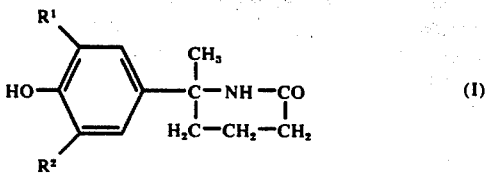

in which $R^1$ and $R^2$, which may be identical or different, each represent a hydrogen or halogen atom or an alkyl or alkoxy group of 1 to 9 carbon atoms.

Preferably, the afore-mentioned alkyl or alkoxy groups have 1 to 6 carbon atoms and are straight-chained or branched. As examples, there may be mentioned the groups methyl, ethyl, propyl, i-propyl, butyl, i-butyl, t-butyl, pentyl and hexyl, as well as methoxy, ethoxy, propoxy, i-propoxy, butoxy, pentoxy and hexoxy. As halogen atoms, chlorine and bromine are preferably used.

The invention furthermore relates to a process for preparing substituted piperidones and to pharmaceutical compositions which consist of, or contain, a substituted hydroxyphenyl-piperidone of the invention.

The process of manufacture according to the invention comprises reacting a $R^1$, $R^2$-substituted phenol with 5-oxohexanenitrile of the formula II

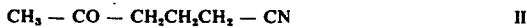

and, if desired, subsequently alkylating or halogenating it at the phenol nucleus. The process is preferably carried out in an acid medium; the pH-value of the reaction medium is, in particular, 1 to 3. The reaction is effected at a temperature in the range of from 0° to 60° C, preferably from 20° to 40° C. The subsequent introduction of an alkyl group is suitably carried out in the presence of Friedel-Crafts catalysts.

The reaction is advantageously carried out in the presence of a catalyst. As catalysts, there are suitable above all mercaptans, in particular linear mercaptans of 1 to 6 carbon atoms, for example methylmercaptan, ethylmercaptan, propylmercaptan and butylmercaptan. The catalyst is used in a quantity of 0.01 to 2%, preferably 0.1 to 0.5 % (referred to the phenol used).

In order to maintain the acid range of the medium, the process of the invention is carried out in the presence of a proton donor. As such are suitable, in particular mono-, di- or tri-basic mineral acids, for example sulfuric acid and phosphoric acid. Gaseous hydrohalic acids, for example hydrochloric acid, are preferably used. Acid ion exchangers are likewise suitable.

As phenols, there are preferably used phenol, 2-alkylphenols, 2-alkoxyphenols, 2,6-dialkylphenols and 2,6-dialkoxyphenols; the monoalkyl- or monoalkoxy-phenols have 7 to 15, preferably 7 to 12 carbon atoms, while the dialkyl- or dialkoxy-phenols have 8 to 24, preferably 8 to 20 carbon atoms.

The molar ratio of phenol to 5-oxohexane-nitrile is from 1:1 to 10:1, preferably from 2:1 to 4:1.

The substituted hydroxyphenol-piperidones of the invention have valuable pharmacological properties; they reduce the triglyceride content in the serum and are, therefore, suitable for the therapy of hyperlipidemia.

Since increased lipid levels in the blood are essential risk factors in the development of cardiac coronary diseases and, on the other hand, increased serum lipid concentrations are also important risk factors in the development of arteriosclerotic disorders, the reduction of increased serum lipid values plays an extraordinarily important role in the prophylaxis and therapy of arteriosclerosis, especially that occurring in the area of the coronary vessels. Thus, the compounds of the invention are useful in the treatment and prophylaxis of arteriosclerosis disorders, especially in the area of the coronary vessels, but also in areas of other vessels.

This hypolipidemic action of the compounds of the invention has been proved on the male rat having a normal serum lipid concentration.

The compounds of the invention are used either alone or in admixture with pharmacologically tolerated carriers and, if desired, together with other active substances. Oral administration is preferred. To make the compounds of the invention suitable for administration, they are brought, per se or in admixture with other known substances, into a form which is appropriate for said administration, for example into the form of granules, tablets, capsules, emulsions, aqueous or oily suspensions or aqueous or oily solutions.

When bringing the compounds of the invention into the form of dry compositions, there may be used, as inert carriers and fillers diluents e.g. magnesium carbonate, talcum or lactose, as granulation and disintegration auxiliary agents e.g. starch or alginic acid, as binders e.g. starch or gelatin, and as lubricating agents e.g. stearic acid, talcum or magnesium stearate. The compositions may be obtained by dry or wet granulation. Moreover, they may be provided with a coatng which retards absorption in the gastro-intestinal tract and thus affords a prolonged action.

The active substance may be incorporated in similar manner into suspensions, syrups or elixirs which contain the usual auxiliary agents. As suspending agents, there may be used, e.g. methyl cellulose, tragacanth or sodium alginate. As wetting agents, there may be used e.g. lecithin or polyoxyethylene stearate. As oily carriers or solvent, there may be used vegetable or animal oils, e.g. peanut oil or sun-flower oil or cod-liver oil. Moreover, the compositions may contain the usual additives such as sweeteners, aromatic substances, dyestuffs or conserving agents.

The daily dose is 0.5 to 3 g and is administered two to three times per day in partial amounts of 0.25 to 1 g, preferably from 250 to 500 mg.

A special use of the compounds of the invention comprises their combination with other active substances. These are, above all antidiabetic agents, e.g. Glycodazine, Tolbutamide, Glibenclamide, Phenformine, Buformine and Metformine, furthermore agents having an action on the circulation in the broadest sense, in particular, however, coronary dilators, e.g. Chromonar and Prenylamine, blood-pressure lowering agents such as Reserpine, α-Methyl-Dopa and Clonidine, geriatric agents, psychopharmacological agents e.g. Chlorodiazepoxide, Diazepame and Meprobamate, as well as weight reducing agents, vitamins and other hypolipidemic agents.

The following Examples illustrate the invention:

EXAMPLE 1

A mixture of 120 g of o-tert.-butylphenol (0.8 mole), 22 g of 5-oxohexanenitrile (0.2 mole) and 0.2 g of ethylmercaptan was saturated with hydrogen chloride gas and stirred for 48 hours at 20° C. When the reaction was completed, the reaction product was dissolved in 1 liter of cyclohexane and the solution was neutralized with a sodium bicarbonate solution. The cyclohexane solution was then washed with water. The solvent was removed and the residue was recrystallized from ethanol. 41 g of 6-(4'-hydroxy-3'-tert.butyl-phenyl)-6-methyl-piperidone-(2) ($C_{16}H_{23}NO_2$) having a melting point of 244° C were obtained.

EXAMPLE 2

A mixture of 122 g of 2,6-dimethylphenol (1 mole), 28 g of 5-oxohexanenitrile (0.25 mole) and 0.2 g of ethylmercaptan was heated to 40° C and a weak stream of hydrogen chloride gas was introduced for 8 hours into the mixture. The batch was then allowed to react for 48 hours at 20° C. The solid reaction product was boiled in acetonitrile, filtered off and washed with acetonitrile. The raw product was recrystallized twice from ethanol. 38 g of 6-(4'-hydroxy-3',5'-dimethylphenyl)-6-methylpiperidone-(2) ($C_{14}H_{19}NO_2$) having a melting point of 227° C were obtained.

EXAMPLE 3

A mixture of 164 g of 2-methyl-6-tert-butylphenol (1 mole), 28 g of 5-oxohexanenitrile (0.25 mole) and 0.2 g of ethylmercaptan was saturated with hydrogen chloride gas at 20° C. After about 48 hours, the viscous reaction product was boiled with acetone, filtered off and washed with acetone. The raw product was recrystallized from ethanol. 60 g of 6-(4'-hydroxy-3'-methyl-5'-tert.butylphenyl)-6-methyl-piperidone-(2) ($C_{17}H_{20}NO_2 : C_2H_5OH$) having a melting point of 203° C were obtained.

EXAMPLE 4

A weak stream of hydrogen chloride gas was introduced for about 6 hours into a mixture of 128 g of 2,6-diisopropylphenol (1 mole), 28 g of 5-oxohexanenetrile (0.25 mole) and 0.2 g of ethylmercaptan at 10° C; the mixture was then stirred for 48 hours at 20° C. The reaction product was boiled with cyclohexane, filtered off and recrystallized from ethanol. 42 g of 6-(4'-hydroxy-3',5'-di-isopropylphenyl)-6-methyl-piperidone-(2) ($C_{18}H_{27}NO_2$) having a melting point 185° C were obtained.

EXAMPLE 5

6-(4'-Hydroxyphenyl)-6-methyl-piperidone-(2)

94 g of phenol (1 mole), 28 g of 5-oxohexanenitrile (0.25 mole) and 0.15 g of ethylmercaptan were heated to 40° C and saturated for about 5 hours with hydrogen chloride gas. For working up, the batch was dissolved in methylene chloride, washed with water to neutrality, the solvent was removed and the residue was recrystallized from ethanol. 31 g of 6-(4'-hydroxy-phenyl)-6-methyl-piperidone-(2) ($C_{12}H_{15}NO_2$) having a melting point of 268° C were obtained.

EXAMPLE 6

250 mg each of the compound obtained according to Example 1 in finely powdered form in admixture with 100 mg each of lactose were filled into hard gelatin capsules of corresponding size. The compounds obtained according to Examples 2, 3, 4 and 5 could likewise be brought in the same manner into a form suitable for administration.

EXAMPLE 7

500 mg of the compound obtained according to Example 1, 200 ml of lactose and 20 mg of ascorbic acid were filled in the manner described in Example 6 into hard gelatin capsules.

EXAMPLE 8

100 g of the compound obtained according to Example 1, 20 g of calcium sulfate and 50 g of cane sugar were mixed and the mixture was granulated with hot 10% gelatin solution. The wet mass was pressed through a U.S. standard sieve of 16 mesh (mesh size 1.19 mm) directly on drying pans. The granules so obtained were dried at 49° C and pressed through a U.S. standard sieve of 20 mesh (mesh size 0.84 mm). These granules were then mixed with 30 g of starch, 10 g of talcum and 6 g of stearine and pressed through a U.S. standard sieve of 60 mesh (mesh size 0.25 mm). They were then pressed into tablets which contained each 250 g of the compound of the invention.

EXAMPLE 9

250 mg each of the compound obtained according to Example 1 were made into a paste with 750 g of peanut oil and filled into soft gelatin capsules. The compounds obtained according to Examples 2, 3, 4 and 5 could likewise be brought into the same form suitable for administration.

EXAMPLE 10

In order to prepare a composition suitable for oral administration, 250 g of placebo granules consisting of 60% by weight of lactose and 40% by weight of starch were combined with 250 g of the compound obtained according to Example 1 and then 30 g of talcum and 20 g of magnesium stearate were added. Tablets were prepared from the mixture on a rotary machine, which then contained each 250 mg of the compound of the invention.

EXAMPLE 11

Tablets were prepared from the following components: ground compound obtained according to Example 1: 250 mg; maize starch: 140 mg; lactose, pulverized; 45 mg; talcum: 30 mg; amylopectin: 30 mg; magnesium stearate: 5 mg.

EXAMPLE 12

A mixture of 550 g of the compound of Example 1, 95 g of maize starch, 44 g of alginic acid and 3.6 g of magnesium stearate was pressed into forms and then ground to granules. The granules were sieved through a U.S. standard sieve of 8 mesh (sieve size 2.38 mm) and combined with 3.4 g of magnesium stearate. The mixture was then pressed into tablets which contained 300 mg of the compound of the invention.

EXAMPLE 13

3.1 g of gum arabic and 1.6 g of gum tragacanth were added to a mixture of 150 g of the compound of Example 1 and 44 g of grain oil. The mixture is combined slowly with a solution of 0.1 g of cethyl-alcohol-polyoxyethyl-condensate, 40 g of cane sugar, 0.025 g of propyl-parahydroxybenzoate and 0.35 g of methyl-parahydroxy-benzoate in 108 g of water. After addition of a flavoring agent and of a dyestuff, the mixture was homogenized on a conventional homogenizer to an emulsion which was suitable for oral administration. This emulsion was filled into vessels.

EXAMPLE 14

A mixture of 500 g of the compound of Example 1, 90 g of maize starch and 7 g of magnesium stearate was pressed into forms. These forms were ground to granules and stirred through a 8 mesh sieve (mesh size 2.38 mm). The granules were then coated with the necessary quantity of 15 g of shellac, 13 g of olive oil and 800 g of ethyl alcohol. After addition of 3 g of magnesium stearate, the mixture was pressed into tablets containing 250 g of active substance.

EXAMPLE 15

The hypolipidemic action of the compounds obtained according to the invention was tested on male rats having a normal serum triglyceride level. For this purpose, the modification of the triglyceride concentration in the serum after a 8 day treatment of the test animals with different daily doses was determined.

The compound to be tested was administered as daily single dose orally with the aid of an esophageal sound. Blood was taken from the test animals prior to the treatment and 20 hours after the last administration and the concentration of triglyceride in the serum was determined according to the method of Eggstein and Kreutz. For comparison, a control group of test animals was used which had received only the solvent.

The modifications of the triglyceride concentrations in the serum caused by the treatment are shown in the following Table. In this Table, the modification of the values of the group treated has been referred to the values of the untreated control group, for which the serum triglyceride concentration has been taken as 100%. Thus, the values indicated represent the percentual modification in the group which had received the compounds of the invention, referred to the placebo group.

Table

| Daily dose (mg/kg) | Modification of the triglyceride concentration in the serum (%) | | | |
|---|---|---|---|---|
| | Example 1 | Example 2 | Example 3 | Example 4 |
| 100 | −42 | −33 | −44 | −62 |
| 32 | −17 | −14 | −22 | — |
| 10 | −20 | − 5 | −29 | −18 |

We claim:

1. A pharmaceutical composition for the treatment of hyperlipidemia, said composition comprising an effective amount of a piperidone compound of the formula

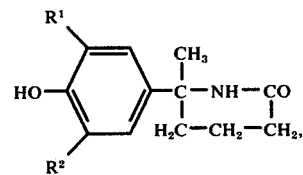

wherein $R^1$ and $R^2$ are both hydrogen, alkyl having 1 to 9 carbon atoms, or alkoxy having 1 to 9 carbon atoms, or wherein one of $R^1$ and $R^2$ is hydrogen and the other is alkyl having 1 to 9 carbon atoms or alkoxy having 1 to 9 carbon atoms.

2. A composition as in claim 1 wherein said piperidone is 6-(4'-hydroxy-3'-methyl-5'-tert. butyl phenyl)-6-methyl-piperidone-(2).

3. A method for lowering the serum lipid level in the treatment of hyperlipidemia, which method comprises administering an effective amount of a piperidone compound of the formula

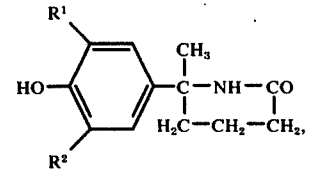

wherein $R^1$ and $R^2$ are both hydrogen, alkyl having 1 to 9 carbon atoms, or alkoxy having 1 to 9 carbon atoms, or wherein one of $R^1$ and $R^2$ is hydrogen and the other is alkyl having 1 to 9 carbon atoms or alkoxy having 1 to 9 carbon atoms.

4. A method as in claim 3 wherein said piperidone is 6-(4'-hydroxy-3'-methyl-5'-tert. butyl phenyl)-6-methyl-piperidone-(2).

* * * * *